United States Patent [19]

Narayanan et al.

[11] Patent Number: 5,156,666
[45] Date of Patent: * Oct. 20, 1992

[54] DELIVERY SYSTEM FOR AGRICULTURAL CHEMICALS

[75] Inventors: Kolazi S. Narayanan, Palisades Park; Ratan K. Chaudhuri, Butler; Manilal Dahanayake, Wayne, all of N.J.

[73] Assignee: ISP Investments Inc., Wilmington, Del.

[*] Notice: The portion of the term of this patent subsequent to Dec. 10, 2008 has been disclaimed.

[21] Appl. No.: 546,014

[22] Filed: Jun. 28, 1990

Related U.S. Application Data

[63] Continuation-in-part of Ser. No. 505,030, Apr. 5, 1990, which is a continuation-in-part of Ser. No. 448,707, Dec. 11, 1989, Pat. No. 5,071,463.

[51] Int. Cl.⁵ .................. A01N 57/00; A01N 43/00; A01N 43/48
[52] U.S. Cl. .................... 71/79; 71/86; 71/88; 71/93; 71/94; 71/100; 71/105; 71/107; 71/118; 71/119; 71/121; 71/124; 514/788
[58] Field of Search ........... 514/408, 424, 936, 946, 514/788; 71/DIG. 1, 93, 86, 88, 94, 100, 105, 107, 118, 119, 121, 124, 79

[56] References Cited

U.S. PATENT DOCUMENTS

| | | | |
|---|---|---|---|
| 3,479,176 | 11/1969 | Forrest | 71/94 |
| 3,882,243 | 5/1975 | Maeda et al. | 514/552 |
| 4,122,170 | 10/1978 | Rajadhyaksha | 514/24 |
| 4,444,762 | 4/1984 | Rajadhyaksha | 514/24 |
| 4,525,199 | 6/1985 | Rajakhyaksha | 71/65 |
| 4,638,026 | 1/1987 | Sambuis | 524/98 |
| 4,762,549 | 8/1988 | Rajadhyaksha | 71/88 |
| 4,840,663 | 1/1989 | Quadranti et al. | 71/93 |

FOREIGN PATENT DOCUMENTS 2128225 12/1972 Fed. Rep. of Germany.

OTHER PUBLICATIONS

Chemical Abstracts (75:109261k) 1971.
Chemical Abstracts (78:80918d) 1973.
Chemical Abstracts (111:111041u) 1989.
Research Disclosure Dec., 1989 "Stable Pesticidal Emulsions".

*Primary Examiner*—Frederick E. Waddell
*Assistant Examiner*—K. Weddington
*Attorney, Agent, or Firm*—Jules Goldberg; Marilyn J. Maue; Joshua J. Ward

[57] ABSTRACT

An emulsifiable concentrate comprising an agriculturally active chemical, a surfactant, and a solvent selected from the group consisting of a first component capable of solubilizing the agriculturally active chemical, a second component capable, in conjnction with the surfactant, to disperse the agriculturally active chemical, and combinations thereof, said first and second being biodegradeable. The inventive concentrate allows for high concentrations of the active ingredient, exhibits excellent stability and produces highly stable compositions upon dilution with water.

16 Claims, No Drawings

DELIVERY SYSTEM FOR AGRICULTURAL CHEMICALS

CROSS-REFERENCE TO OTHER APPLICATIONS

This application is a continuation-in-part of application Ser. No. 505,030, filed Apr. 5, 1990, which, in turn, is a continuation-in-part of application Ser. No. 07/448,707, filed Dec. 11, 1989, now U.S. Pat. No. 5,071,463, (hereinafter, the Parent Applications) the contents of all of which are incorporated herein by reference.

BACKGROUND OF THE INVENTION

I. Field of the Invention

The invention relates to a delivery system for agriculturally active chemicals. More particularly, the invention relates to an emulsifiable concentrate of difficult to dissolve agricultural chemicals making use of biodegradeable solvents.

II. Description of the Prior Art

Agricultural chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into an emulsion, it is difficult to maintain the emulsified state. This makes it difficult to maintain a uniform formulation, particularly, when the formulation is diluted with water for application to the plants.

Typically, for example, the agriculturally active ingredient is mixed with one or more of a variety of conventional solvents and an emulsifying agent to form a concentrate. This concentrate may be an emulsion, suspension, or solution. The concentrate is then stored until it is transported to the site of use or may simply be transported and stored at the site of use. In any event, the concentrate normally will undergo some period of storage until it is ready for use. Understandably, it is most desirable to be able to transport the agriculturally active ingredient at the highest concentration possible so as to minimize the volume of material which need be transported. By the same token, however, at the use site, it is normally not feasible to admix ingredients together or to process them other than to dilute the concentrate with water. Accordingly, it is important that the concentrate emulsify easily, i.e., exhibit good "bloom", upon the addition of water. In addition, at the use site, it is often necessary to store the diluted concentrate for extended time periods until the actual application to the plants. Consequently, it is important that the diluted form of the concentrate exhibit good stability with respect to the uniformity of the emulsion and to avoid precipitation of the active ingredients. If non-uniformity or precipitation occurs in the diluted form, then non-uniformity will result in the application of the diluted formulation to the plants.

An attempt to provide concentrates of agriculturally useful chemicals is disclosed in South African Patent Application No. 695,393, filed Jul. 25, 1969. This application is directed to the formulation of a concentrate substantially water-insoluble pesticides for agricultural use. The pesticides, either in oil or solid form, are mixed with pyrrolidones having a hydrogen or a lower alkyl group containing from 1 to 4 carbon atoms attached to the nitrogen atom of the pyrrolidone ring. The application discloses that concentrated solutions of difficult to dissolve pesticides could be formulated and that such concentrates exhibited good stability. The concentrates utilized are those containing the pesticidal active ingredient, the particular lower alkyl pyrrolidone, a co-solvent which is usually a common organic solvent, such as, an aromatic including xylene, methylated and polyalkylated naphthalenes and aliphatic solvents, and a dispersing or emulsifying agent, such as, a surfactant, including polyoxyethylene alkylphenols, polyoxyethylene fatty esters, polyoxyethylene sorbitan fatty esters which may be blended with oil-soluble sulfonates, calcium and aminosulfonate salts, and the like.

This prior art does not offer a solution to the problem arising from the difficulty in maintaining the stability of the emulsion after the concentrate is diluted with water. Consequently, unless the diluted form of the concentrate is used immediately after emulsification, it is difficult to provide a stable diluted formulation for application to the plants.

In addition, for such agricultural uses, it is desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate. Moreover, many organic solvents which have been used in the past, even those exhibiting relatively low toxicities, are not biodegradeable and thus remain as a pollutant.

SUMMARY OF THE INVENTION

We have discovered a novel emulsifiable concentrate of an agriculturally active chemical, which concentrate provides, upon dilution, a highly stable emulsion and avoids precipitation of the active ingredient on extended storage. In addition, the inventive emulsifiable concentrates may contain relatively high concentrations of the agriculturally active ingredient, sometimes referred to as a "loading", making it advantageous from both economic and handling viewpoints. Also, the concentrates of the present invention utilize organic materials which do not pose environmental problems either in use or handling, and are biodegradeable.

More particularly, the emulsifiable concentrate of the present invention is composed of an agriculturally active chemical, a surfactant, and a hydrophobic solvent having the following Hansens' solubility parameters:

Dispersive component from about 56 to 75%;
Polar component from about 8 to 24%; and
H-bonding component of from about 10 to 30%.

This solvent should also have surfactant properties and act as a non-ionic surfactant with an HLB value ranging from about 2 to 8.

For a discussion of the solubility parameters, see *C.R.C. Handbook of Solubility Parameters and Other Cohesion Parameters*, Allan F. M. Barton, 1983, Table 9, p, 167–170.

In another embodiment, the inventive emulsifiable concentrate is composed of an agriculturally active chemical, a surfactant, and a solvent having a first component, a second component (the hydrophobic solvent), or combinations thereof. In the inventive compositions, no diluent, as defined in the Parent Applications, is used.

The first component of the solvent is selected from those compounds which have a sufficiently high hydrophilic property to solubilize the agriculturally active chemical. Preferably, the first component will have the following Hansens' solvent parameters:

Dispersable component from about 40 to 50%;
Polar components of from about 25 to 40%; and
H-bonding component of 10 to 30%.

The second component is a hydrophobic solvent having the following Hansens' solubility parameters:

Dispersable component from about 56 to 75%;
Polar component from about 8 to 24%; and
H-bonding component of from about 10 to 30%.

An important advantage of these embodiments is that the solvent used is completely biodegradeable.

DESCRIPTION OF THE PREFERRED EMBODIMENT

As used herein, the term "agriculturally active chemical" includes compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, and the like, as well as any other chemicals having properties which are suitable for agricultural uses in terms of application to plants or domestic uses for controlling insects and pests. Particularly, such chemicals would normally take the form of water-immiscible or oily liquids and/or solids which is substantially insoluble in water. By the term "substantially insoluble", it is meant that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithiophosphates. (See *Agricultural Chemicals*, Book I, *Insecticides*, 1989 Revision by W. T. Thomson, Thomson Publications.) Typical of the insecticides are:

| | |
|---|---|
| cyclocompounds: | 6,7,8,9.10,10-hexachloro-1,5,5a,6,9,9a-hexahydro-6,9-methano-2,4,3-benzodioxathiepin-3-oxide |
| carbamates: | 2-isopropyl phenyl-N-methyl carbamate; 2-(1,3-dioxolan-2yl) phenylmethyl carbamate; 2,3-isopropylidine dioxyphenyl methyl carbamate; |
| animal and plant derivatives: | chlorinated hydrocarbons derived from Southern pine; naturally occurring lactone glycoside; |
| synthetic pyrethroids: | (±) α-cyano-3-phenoxybenzyl (±) cis,trans 3-(2,2-dichlorovinyl)-2,2-dimethyl cyclopropane carboxylate; (±) cyano (3-phenoxyphenyl methyl (±)-4-(difluoromethyoxy) α-(1-methylethyl) benzene acetate; |
| phenoxy compounds and non-phosphate: | 2,2-bis(p-methoxy phenyl)-1,1,1,trichloroethane; 1,3,5,tri-n-propyl-1,3,5-triazine-2,4,6 (1H,3H,5H) trione; ethyl (2E,4E)-3,7,11-trimethyl-2,4-dodeca dienoate; 1-decycloxy 4-[(7-oxa-oct-4-ynyl)]-oxybenzene; |
| organic phosphates: | dimethyl phophate ester of 3-hydroxy-N,N-dimethyl-cis-crotonamide; 2-chloro-1-(2,4-dichloro phenyl) vinyl diethylphosphate; 4-(methyl thio) phenyl dipropyl phosphate; |
| thiophosphates: | 0,0-diethyl-0-4-nitrophenyl phosphorothioate; 0,0-diethyl-0-(2,isopropyl-6-methyl-5-pyrimidinyl) phosphorothioate; 2-diethylamino-6-methyl pyrimidine-4-yl dimethyl phosphorothioate; |
| dithiophosphates: | 0,0-dimethyl phosphorodithioate ester of diethylmercapto succinate; 0-ethyl-S-phenyl ethyl phosphorodithioate. |

Typical herbicides include phenoxy compounds, benzoic, acetic, and phthalic acids, aniline derivatives, nitriles, amides, acetamides, anilides, carbamates, thiocarbamates, and heterocyclic nitrogen derivatives, e.g., triazines, pyridines, pyridazones, picolinic acid, and urea derivates and phosphates. (See *Agricultural Chemicals*, Book II, *Herbicides*, 1986–87 Edition, W. T. Thomson, Thomson Publications, Fresno, Calif. 93791.) Exemplary of the above compounds are:

| | |
|---|---|
| phenoxy compounds: | 2,4-Dichlorophenoxy acetic acid 2,4,5-trichloro phenoxyacetic acid; 4-(2,4-dichlorophenoxy) butyric acid; S-ethyl 2 methyl-4-chlorophenoxy-thioacetate; 2-methyl-4-chloro-phenoxy acetic acid; methyl 5-(2,4-dichloro-phenoxy)-2-nitrobenzoate; |
| benzoic and acetic acids of phthalic compounds: | 3,6-dichloro-o-anisic acid 4-chloro-2-oxo benzothiazolin-3-yl acetic acid; N-1-Naphthyl-phthalamic acid |
| nitriles and aniline derivatives: | 3-5-dibromo-4-hydroxybenzo-nitrile; α,α,α,trifluoro-2,6-dinitro-N,N-dipropyl-p-tolinidine; |

| | |
|---|---|
| amides, acetamides, anilides: | N-(1-ethylpropyl)-2,6-dinitro-3,4-xylidine; N,N-diethyl-2-(1-naphthalenyl oxy)-propionamide; 2,6-dimethyl-N-2′ methoxy-ethyl-chloro-acetanilide; 3′,4′-dichloro-propionanilide; α-chloracetic-N-(3,5,5-trimethyl-cyclohexen-1-yl)-N-isopropylamide; 4-benzyl-N-isopropyl trimethyl acetamide; |
| thiocarbamates: | S-ethyl dipropyl thiocarbamate; |
| urea derivatives: | 3-(5-tert-butyl-3-isoxazoyl)-1,1-dimethyl urea; N-(2,6-trifluoro-benzoyl)-N′-[2,5-dichloro-4-(1,1,2,3,3,3-hexa-fluoropropyloxy) phenyl] urea; |
| pyrrolidone derivatives: | 1-(m-trifluoro methyl phenyl)-3-chloro-4-chloromethyl-2-pyrrolidone; |
| amino acid derivatives: | methyl N-benzoyl-N-(3-chloro-4-fluorophenyl)-DL alarinate; N-chloroacetyl-N-(2,6-diethyl phenyl)-glycine ethyl ester; |
| carbamates: | isopropyl-m-chlorocarbanilate; 3-ethoxy (carbonyl aminophenyl)-N-phenyl carbamate; |
| heterocyclics: | 4-amino-3,5-dichloro-6-fluoro-2-pyridyloxy acetic acid; 4-(1,2-Dimethyl-N-propyl amino)-2-ethyl amino-6-methyl thio-S-triazine; 2-[4,5-dihydro 4-methyl-4-(1-methyl ethyl)-5-oxo-1 H-imidazoyl-2yl]-3-byridinecarboxylic acid; 2-[3,5-dichlorophenyl]-2-(2,2,2-trichloroethyl) oxinane; butyl-9-hydro-fluorene-(9)-carboxylate; 2-[1-(ethoxy imino) butyl]-3-hydroxy-5-(2H-tetra hydro thiopyran-3-yl)-2-cyclohexene-ione; 2-(2 chlorophenyl) methyl-4,4-di-methyl-3-iso oxazolidinone; |
| phosphates: | O-ethyl-O-(3-methyl-6-nitro phenyl) N-sec-butyl phosphoro thio amidate. |

Typical fungicides include (See *Agricultural Chemicals*, Book IV, *Fungicides*, 1989 Revision, W. T. Thomson, Thomson Publications, Fresno, Calif. 93791):

| | |
|---|---|
| organic compounds: | 2,5-dimethyl-N-Cyclohexyl-N-methoxy-3-furan carboxamide; 5-Ethyoxy-3-trichloromethyl-1,2,4-thiadiazole; 3-(2-methyl piperidino) propyl 3,4-dichlorobenzoate; N,N′-(1, 4-piperazinediyl bis (2,2,2-trichloro) ethylidene) bis formamide; Tetramethyl thiuram disulfide; O-Ethyl-S,S,diphenyl-dithiophosphate; 5,10-dihydro-5, 10-dioxo naphtho (2,3,9)-p-dithiin-2,3-dicarbo-nitrile; 2-(Thiocyano methyl thio) benzothiazole; α-2-(4-chlorophenyl) ethyl]-α-(1,1-dimethyl ethyl)-1 H-1,2,4-triazole-1-ethanol; |
| morpholines: | N-trideoyl-2,6-dimethyl morpholine; 4-N-dodecyl-2,6-dimethyl morpholine. |

Typical fumigants, growth regulators, repellants, and rodenticides include (See *Agricultural Chemicals*, Book III, *Fumigants*, 1988-1989 Revision, W. T. Thomson, Thomson Publications, Fresno, Calif. 93791):

| | |
|---|---|
| growth regulants: | 1,2 Dihydro-6-ethyoxy-2,2,4-trimethylquinoline; (2-chloroethyl) phosphoric acid; 4-[acetamino) methyl]-2-chloro-N (2,6-diethyl phenyl acetamide; Benzoic acid,3,6 dichloro-2-methoxy,2-ethoxy-1-methyl-2-oxo ethyl ester; |
| repellants: | O,O-dimethyl-O-[(4-methyl thio)-m-tolyl] phosphorothioate; Tetriary butyl-sulfenyl dimethyl dithio carbamate; |
| seed softener: | 2-chloro-6-(trichlomethyl) pyridine; 5-ethoxy-3-trichloromethyl-1,2,4-thiadiazole; N-phenyl-N′-1,2,3-thiadiazol-5-yl urea. |

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: O,O-diethyl-O-2,5-dichloro-4-bromophenyl thionophosphate,
N-(2-mercaptoethyl) benzene-sulfenamide (BETASAN ®),
Isobornyl Thiocyanoacetate (Thanite ®),
Ioxynil ester of octanoic acid,
Molinate S-ethyl hexahydro-1H-azepine-1-carbothioate,
PP 511 O,O-dimethyl-(2-diethylamine 4-methyl-6-pyrimidinyl) carbamate,
PP 211 O,O-diethyl O-(2-diethylamine-4-methyl-6-pyrimidinyl) phosphorocarbamate,
Chlordane,
5-Ethoxy-3-(trichlorometyl)-1,2,4-thiadiazole (TERRAZALE ®),
Ethyl-s-s-dipropyl-phosphodithioate (MOCAP ®),
S-Ethyl dipropylthiocarbamate (EPTAM ®),
S-Ethyl diisobutylthiocarbamate (SUTAN ®),
S-n. propyl-di-n-propylthiocarbamate (VERNAM ®),
S-propyl butylethylthiocarbamatae (TILLAM ®), S-ethyl ethylcyclohexylthiocarbamate (RO-NEET®), Malathion (S-(1,2-dicarboxyethyl)-O,O-dimethyl phosphorodithioate), Diazinon (O,O-diethyl,O-(2-isopropyl-4-methyl-6-pyrimidinyl) phosphorothioate, O-Ethyl-S-phenyl-ethylphosphonodithioate (DYFONATE®), Toxaphene (Octachlorocamphene), Bromoxynil (3,5-dibromo-4-hydroxy benzonitrile ester of n.octanoic acid, 2-chloro-N-2,6-diethylphenyl-N-methoxymethylacetamide (LASSO®), Diallate S-2,3-dichloroallyl N,N-diisopropylthiolcarbamate, Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea
Atrazine (2-chloro-4-ethylamino-6 isopropylamino-s-triazine) Simazine (2-chloro-4,6,-bis (ethylamino)-s-triazine)
Dodine (n-dodecylguanidine acetate)
Thiram (tetramethylthiuram disulfide)
N-(mercaptomethyl)phthalimide s-(o,o dimethyl-phosphorodithioate) (IMIDAN®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylamiline) (2,3 dihydro-5-carboxanilido-6-methyl-1,4-oxathiin) (VITAVAX®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Carbaryl: 1-naphthyl-N-methylcarbamate
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149: 5-n-butyl-2 ethylamino-4-hydroxy-6 methyl-pyrimidine*

* Manufactured by Imperial Chemical Industries Limited

C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl)-N-methylurea
NIA 11092 1,1-dimethyl-3-[3-(n-t-butyl carbamyloxy)phenyl]urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlororphenyl)propionamide
Pyriclor 2,3,5-trichloro-4-pyridinol
Solan 3'-chloro-2-methyl-p-volerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl-)acetamide
Cypromid 3',4'-dichlorocyclopropane carboxanilide
Fenuron NN-dimethyl-N'phenylurea
Chlorbromuron N'-(4-bromo-3-chlorophenyl)-N-methoxy-N-methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropylaniline
PP 493 2,6-difluoro-3,5-dichloro-4-hydroxy pyridine
CNP 2,4,6-trichlorophenyl-4'-nitrophenyl ether
Pentachloro nitrobenzine
1-(butile carbamoyl)-2-benzimidazol carbamic acid, methyl ester (BENLATE®)

Typical examples of first components suitable for use in the solvent are alkylpyrrolidones having from 1 to 4 carbon atoms in the alkyl group, cyclic lactones, e.g., gamma-butyrolactones, lower alkyl cyclic carbonates, i.e., ethylene carbonate, propylene carbonate, butylene carbonate, lower akylimidazolone, e.g., N-N,dimethylimidazolone, lower alkylamides of formic acid and acetic acid, e.g., dimethyl formamide and dimethylacetamide, and lower alkyl sulfoxides, e.g., dimethylsulfoxide. (The term "lower alkyl" in these examples means one or two carbons.) Mixtures of these may also be used as the first component.

Examples of appropriate second components or hydrophobic solvents include alkylpyrrolidones having an alkyl portion containing from 6 to 14 carbon atoms, e.g., octylpyrrolidone, dodecylpyrrolidone, or N-(2'-ethylhexylpyrrolidone), alkyl gamma-butyrolactones, alkyl cyclic carbonates and combinations thereof, wherein the alkyl chains contain from 6 to 14 carbon atoms. The alkyl portion may be distributed at one or more sites on the ring so long as one portion contains at least 6 carbon atoms and the total number of alkyl carbon atoms does not exceed 14. Preferred 6 to 14 carbon alkyl portions are composed of straight chains. Branched or cyclic alkyl portions may also be used.

Preferably, the first component is selected from the group consisting of pyrolidones having the formula

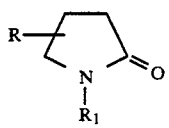

wherein R is hydrogen or lower alkyl having from 1 to 4 carbon atoms and $R_1$ is lower alkyl having from 1 to 4 carbon atoms.

The hydrophobic solvent or second component is preferably selected from pyrrolidones having the formula

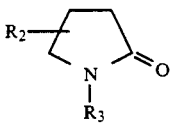

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14.

In the inventive composition, the amount of solvent is in the range from about 40 to 90%.

The inventive composition also contains one or more additional emulsifier(s) or surfactant(s) which is generally selected on a case by case basis in order to optimize the solubility and stability of the emulsion. Typically, such emulsifiers include ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines. Anionic surfactants may be used as the emulsifier and include phosphate esters and their salts, alkyl sulfonamides, salts of sulfated nonylphenoxypoly(ethyleneoxy) ethanol, salts of alkylbenzene sulfonates, salts of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, *Emulsifiers and Detergents* (1989), published by McCutcheon's Division of M. C. Publishing Co., Glen Rock, N.J.) Generally, the amount of emulsifier (surfactant) is from about 1 to 25% based on the total weight of the composition.

The agriculturally active chemical (sometimes referred to herein as AAC) concentration should be as high as possible so long as it does not precipitate out upon dilution of the concentrate with water for a reasonable period of time and achieves the desired effect. Precipitation (crystal formation) on standing not only depletes the solution of AAC, it can also lead to fouling of application equipment, i.e., sprayers, etc. With the present invention, it is possible to obtain concentrates with agriculturally active chemical concentrations in excess of 5 weight percent which form a stable emulsion upon being diluted with water. Depending on the particular agriculturally active chemical, the concentration of the AAC is from about 5 to 25% based on the total weight of the composition before dilution.

The final use concentration values depend on the AAC. However, it is important that upon dilution, the diluted form remain stable for a time sufficient to allow it to be applied. This, of course, will vary with the schedule for the application in the field. Normally, the diluted concentrate is applied within four hours of dilution. It is possible, however, due to equipment and personnel delays, that a standing period of up to 24 hours may be encountered. With the present invention, prolonged stability of the emulsified concentrate, as is, as well as in the diluted form is obtained. In particular, the emulsified concentrate in accordance with the present invention can be diluted to final use concentrations in the range from about 10 ppm to 2 percent, depending on the specific AAC, without any adverse effects, and specifically, precipitation of the AAC from the solution.

The following examples illustrate the present invention*:

In the examples, all compositional percentages are percent by weight of the total composition unless otherwise indicated.

A series of experiments was carried out wherein the type and amount of agriculturally active chemical, hydrophobic solvent, and other components were varied. The samples were evaluated for ease of emulsion and emulsion stability by measuring the amount of separation before and after mixing. The compositions used and results obtained are set forth in the tables that follow.

EXPERIMENTAL PROCEDURE

Formulations

Formulations were prepared by weighing the exact proportion of ingredients and mixing them together in a bottle. The solvents were weighed in first. The AAC was dissolved completely in the solvent system followed by addition of the wetting agent or emulsifying agent. Typically, about 10g of each of the formulations was prepared.

The contents were stirred well in an automatic rocking shaker for about 30 minutes when the AAC dissolved completely. The samples thus prepared were evaluated for freeze-thaw stability on storage and ease of emulsification and emulsion stability on dilution. For dilution, 2 grams of concentrate were diluted to 50 grams using World Health Organization (WHO) standard (6 g of $CaCl_2$ and 2.78 g of $MgCl_26H_2O$ dissolved in 20 L) hard water having a hardness of 342 ppm expressed as $CaCO_3$ equivalent.

Freeze-Thaw Stability

The concentrates were stored for a period of 24 hours in the cold (temperature 5° C.) in a refrigerator and taken out and thawed to room temperature and then stored at 55° C. in an oven for a period of 24 hours. The alternate storage in the cold (5° C.) and warm condition at 55° C. was repeated for three cycles. Any separation during the storage was recorded. A concentrate is "stable" if there is no substantial separation after the 24 hour cycles at each temperature. All of the solutions exemplified hereinafter exhibited stability according to this test between the temperatures of 5° C. and 55° C. Some of the solutions were even stable at a lower range of −5° C.

Evaluation of Emulsion Stability and Ease of Emulsification

A Nessler tube (1.8 cm diameter; 28 cm long) was filled with an appropriate quantity (47–48 g) of WHO water. Using a serological pipette, 0.5–2.5 g of emulsion concentrate was dropped into the Nessler tube containing 47.5–49.5 g water. The initial bloom was observed at zero time without stirring and the quality of the bloom was graded by visual appearance as shown below. The Nessler tube was stopped and inverted 20 times; the bloom was again recorded and so also stability as judged by volume or height of the sedimentation (cream/ppt/oil) followed at different intervals of time: 0, 1 hour, 2 hours, up to 24 hours.

Stability of Diluted Concentrate

The composition of the concentrate (EC) diluted with water was considered "stable" if at EC concentrations of from 0.2 to 1%, the composition after mixing (twenty inversions) exhibited two mm or less cream and no oil in one hour. Both top and bottom should be checked.

| Bloom: | Excellent | Thick emulsion cloud with no separation |
|---|---|---|
| | Good | Emulsion cloud may be thin, or may exhibit trailing, small number of oil droplets within cloud |
| | Poor | Many oil droplets within cloud, some droplets separate from cloud |

Each of the emulsifiable concentrates thus prepared were analyzed for ease of emulsification (bloom) upon addition of water and after twenty inversion of the sample as well as emulsion stability upon dilution with water. The composition of the samples and the results of the analysis are set forth in the following tables.

Crystal Formation Studies

A number of the samples were evaluated for precipitation of AAC, i.e., crystal growth over varying time periods. This was done using the following techniques:

1. The diluted sample was placed in a 100 ml beaker and stirred continuously. Aliquots were removed at 1, 4, 7, and/or 24 hour intervals and examined under 250 x magnification, using a 2×2 mm slide, which provided 1500 separate viewing areas. The number of crystals, if any, in ten different viewing areas were counted and averaged. If no crystals were found, second and third aliquots were examined.

2. The remaining portion of the diluted sample was passed through U.S. Standard screens (60, 100 and 250 mesh) and sediment retained is reported.

3. The diluted sample was allowed to stand without stirring for 24 hours and inverted twenty times. An aliquot of the inverted sample was examined under 250× and the results reported as above. The reamining portion was passed through screens and retained sediment reported.

The results for the crystal growth studies are reported as follows:

0 means no crystals
\* means <10 crystals/view area
\*\* means 10–100 crystals/view area
\*\*\* means 100–1000 crystals/view area
\*\*\*\* means >1000 crystals/view area The components set forth in the Tables are referred to by their commercial names for purposes of brevity. The chemical nomenclature of the materials is as follows:

| | |
|---|---|
| LP-100 | N-octylpyrrolidone |
| LP-300 | N-dodecylpyrrolidone ($C_{12}$ chain) |
| LP-940 | N-octadecylpyrrolidone ($C_{18}$ chain) |
| Gafac RM 710 | Poly(oxy-1,2-ethanediyl)α-(dinonylphenyl)-omega-hydroxy-phosphate. |
| Igepal CO-630 | Ethoxylated nonyl phenol containing 9 EO units |
| Thidiazuron | 1-phenyl-3-(1,2,3-thiadiazol-5-yl)urea |
| Gafac RE-610 | Poly(oxy-1,2-ethanediyl)α-(nonylphenyl)-omega-hydroxy-phosphate. |
| Silwet L-77 | (Silwet copolymer L-77) nonionic organo silicone (Union Carbide) |
| Silwet L-7607 | (Silwet copolymer L-7607) nonionic organo silicone (Union Carbide) |
| Pegol L-31 | Ethoxylated polyoxy propylene |

In the tables, SUPER refers to the upper layer on separation and PCPT refers to the bottom layer.

TABLE 1

| Run No. | 1 | 2 | 3 | 4 | 5 | 6 | 7 | 8 |
|---|---|---|---|---|---|---|---|---|
| Composition wt. % | | | | | | | | |
| N-methyl-pyrrolidone (M-Pyrol) | 0 | 0 | 75 | 0 | 0 | 0 | 0 | 0 |
| N-octyl-pyrrolidone (LP-100) | 75 | 0 | 0 | 0 | 67.5 | 60 | 45 | 30 |
| N-dodceyl-pyrrolidone (LP-300) | 0 | 75 | 0 | 0 | 7.5 | 15 | 30 | 45 |
| Aromatic oil (Exxon 200) | 0 | 0 | 0 | 75 | 0 | 0 | 0 | 0 |
| Cocoyl-pyrrolidone | 0 | 0 | 0 | 0 | 0 | 0 | 0 | 0 |
| Gafac RE-610 | 10 | 10 | 10 | 10 | 10 | 10 | 10 | 10 |
| AAC: thidiazuron | 15 | 15 | 15 | 15 | 15 | 15 | 15 | 15 |
| Solubility at 23°C. | S | PS | IS | IS | S | S | S | S |
| Results:\*\* | | | | | | | | |
| Bloom: | | | | | | | | |
| 0 time | poor | NA | NA | NA | poor | poor | poor | poor |

TABLE 1-continued

| | | | | | | | | | | | | | | | |
|---|---|---|---|---|---|---|---|---|---|---|---|---|---|---|---|
| after 20 turns | excellent | | NA | | NA | | NA | | excellent | | excellent | | excellent | | excellent | |
| Solids, creams, or oil. mm: | SU-PER | PCPT | SU-PER | PCPT | SU-PER | PCPT | SU-PER | PCPT | SU-PER | PCPT | SU-PER | PCPT | SU-PER | PCPT | SU-PER | PCPT |
| 0 time | 0 | 0 | NA | NA | NA | NA | NA | NA | 0 | 0 | 0 | 0 | 0 | 0 | 0 | 0 |
| 1 hour | 0 | 0 | NA | NA | NA | NA | NA | NA | 0 | 0 | 0 | 0 | 0 | 0 | 0 | 0 |
| 2 hours | 0 | 0 | NA | NA | NA | NA | NA | NA | 0 | 0 | 0 | 0 | 0 | 0 | 0 | 0 |
| 4 hours | 0 | 0 | NA | NA | NA | NA | NA | NA | 0 | 0 | 0 | 0 | 0 | 0 | 0 | 0 |
| 24 hours | 0 | 6 | | | | | | | 12 | 0 | 12 | 0 | 8 | 0 | 8 | 0 |
| After 24 hour standing filtered through screen | | | | | | | | | | | | | | | | |
| 60 mesh | — | | NA | | NA | | NA | | — | | — | | — | | — | |
| 100 mesh | — | | NA | | NA | | NA | | — | | — | | — | | — | |
| 250 mesh | — | | NA | | NA | | NA | | — | | — | | — | | — | |

| Run No. | 9 | 10 | 11 | 12 | 13 | 14 | 15 | 16 |
|---|---|---|---|---|---|---|---|---|
| Composition wt. % | | | | | | | | |
| N-methyl-pyrrolidone (M-Pyrol) | 0 | 0 | 15 | 22.5 | 30 | 15 | 15 | 22.5 |
| N-octyl-pyrrolidone (LP-100) | 15 | 37.5 | 45 | 45 | 45 | 60 | 45 | 52.5 |
| N-dodceyl-pyrrolidone (LP-300) | 60 | 37.5 | 0 | 0 | 0 | 0 | 15 | 0 |
| Aromatic oil (Exxon 200) | 0 | 0 | 15 | 7.5 | 0 | 0 | 0 | 0 |
| Cocoyl-pyrrolidone | 0 | 0 | 0 | 0 | 0 | 0 | 0 | 0 |
| Gafac RE-610 | 10 | 10 | 10 | 10 | 10 | 10 | 10 | 10 |
| AAC: thidiazuron | 15 | 15 | 15 | 15 | 15 | 15 | 15 | 15 |
| Solubility at 23°C. | S | S | IS | IS | IS | IS | IS | IS |

Results:*

| | | | | | | | | | | | | | | | | |
|---|---|---|---|---|---|---|---|---|---|---|---|---|---|---|---|---|
| Bloom. | | | | | | | | | | | | | | | | |
| 0 time | poor | | poor | | NA | | NA | | NA | | NA | | NA | | NA | |
| after 20 turns | excellent | | excellent | | NA | | NA | | NA | | NA | | NA | | NA | |
| Solids, creams, or oil. mm: | SU-PER | PCPT | SU-PER | PCPT | SU-PER | PCPT | SU-PER | PCPT | SU-PER | PCPT | SU-PER | PCPT | SU-PER | PCPT | SU-PER | PCPT |
| 0 time | 0 | 0 | 0 | 0 | NA | NA | NA | NA | NA | NA | NA | NA | NA | NA | NA | NA |
| 1 hour | 0 | 0 | 0 | 0 | NA | NA | NA | NA | NA | NA | NA | NA | NA | NA | NA | NA |
| 2 hours | 0 | 0 | 0 | 0 | NA | NA | NA | NA | NA | NA | NA | NA | NA | NA | NA | NA |
| 4 hours | 0 | 0 | 0 | 0 | NA | NA | NA | NA | NA | NA | NA | NA | NA | NA | NA | NA |
| 24 hours | 7 | 0 | 8 | 0 | | | | | | | | | | | | |
| After 24 hour standing filtered through screen | | | | | | | | | | | | | | | | |
| 60 mesh | — | | — | | NA | | NA | | NA | | NA | | NA | | NA | |
| 100 mesh | — | | — | | NA | | NA | | NA | | NA | | NA | | NA | |
| 250 mesh | — | | — | | NA | | NA | | NA | | NA | | NA | | NA | |

S = soluble;
IS = insoluble;
PS = hazy, mostly soluble
— means no sediment;
+ means trace;
++ means more than trace < 1%;
+++ means 1-5%
**2.5 g of concentrate were diluted with standard H₂O to 50 g.

TABLE 2

| Run No. | 17 | 18 | 19 | 20 | 21 | 22 |
|---|---|---|---|---|---|---|
| Composition wt. % | | | | | | |
| N-methyl-pyrrolidone (M-Pyrol) | 75 | 0 | 0 | 37.5 | 0 | 37.5 |
| N-octyl-pyrrolidone (LP-100) | 0 | 75 | 0 | 0 | 37.5 | 37.5 |
| N-dodceyl-pyrrolidone | 0 | 0 | 75 | 37.5 | 37.5 | 0 |

TABLE 2-continued

| Run No. | 17 | | 18 | | 19 | | 20 | | 21 | | 22 | |
|---|---|---|---|---|---|---|---|---|---|---|---|---|
| (LP-300) | | | | | | | | | | | | |
| Gafac RE-610 | 10 | | 10 | | 10 | | 10 | | 10 | | 10 | |
| AAC: | 15 | | 15 | | 15 | | 15 | | 15 | | 15 | |
| Triazol derivative | | | | | | | | | | | | |
| Results:** | | | | | | | | | | | | |
| Bloom: | | | | | | | | | | | | |
| 0 time | fair | | poor | | fair | | fair | | poor | | fair | |
| after 20 turns | excellent | | excellent | | excellent | | excellent | | excellent | | excellent | |
| Solids, creams or | SUPER | PCPT | SUPER | PCPT | SUPER | PCPT | SUPER | PCPT | SUPER | PCPT | SUPER | PCPT |
| oil, mm: | | | | | | | | | | | | |
| 0 time | 0 | 16 | 0 | 0 | 35 | 2 | 0 | 2 | 4 | 0 | 0 | 1 |
| 4 hours | 0 | 19 | 10 | 0 | 42 | 0 | 0 | 3 | 9 | 0 | 0 | 5 |
| 24 hours | 0 | 14 | 14 | 10 | 35 | 0 | 7 | 3 | 35 | 0 | 4 | 5 |
| Crystal Growth*** | ** | | 0 | | 0 | | * | | 0 | | * | |
| After 24 hour standing filtered through screen | | | | | | | | | | | | |
| 60 mesh | ++ | | − | | − | | + | | − | | + | |
| 100 mesh | +++ | | − | | − | | − | | − | | − | |
| 250 mesh | +++ | | − | | − | | − | | − | | − | |

− means no sediment;
+ means trace;
++ means more than trace < 1%;
+++ means 1-5%;
++++ means >5%
**2.5 g of concentrate were diluted with standard H₂O to 50 g.
***Crystal growth observed under 250× after 24 hours standing and 20 inversions.

TABLE 2A

MICROSCOPIC CRYSTAL GROWTH OBSERVATION FOR SELECTED FORMULATIONS

| Run No. | 17 | 18 | 19 | 20 | 21 | 22 |
|---|---|---|---|---|---|---|
| Microscopic observation under stirring for crystal growth, 250× Time: | | | | | | |
| 0 hour | | 0 | | 0 | | |
| 1 hour | | 0 | | ** | | |
| 4 hours | | 0 | | ** | | |
| 24 hours | | 0 | | *** | | |
| After 24 hour stirring filtered through screen | | | | | | |
| 60 mesh | | − | | − | | |
| 100 mesh | | − | | − | | |
| 250 mesh | | − | | + | | |

TABLE 3

| Run No. | 23 | 24 | 25 |
|---|---|---|---|
| Composition wt. % | | | |
| N-methyl-pyrrolidone (M-Pyrol) | 0 | 0 | 0 |
| N-octylpyrrolidone (LP-100) | 65 | 0 | 32.5 |
| N-dodecyl-pyrrolidone (LP-300) | 0 | 65 | 32.5 |
| Gafac RE-610 | 15 | 15 | 15 |

TABLE 3-continued

| Run No. | 23 | | 24 | | 25 | |
|---|---|---|---|---|---|---|
| AAC: | 20 | | 20 | | 20 | |
| Triazine derivative | | | | | | |
| Solubility at 23° C. | S | | IS | | S | |
| Results:** | | | | | | |
| Bloom: | | | | | | |
| 0 time | fair | | NA | | fair | |
| after 20 turns | excellent | | NA | | excellent | |
| Solids, creams or oil, mm: | SU-PER | PCPT | SU-PER | PCPT | SU-PER | PCPT |
| 0 time | 0 | 0 | NA | NA | 0 | 0 |
| 1 hour | 0 | 8 | NA | NA | 0 | trace |
| 4 hours | 35 | 9 | NA | NA | 1 | 2 |
| 24 hours | 40 | 10 | NA | NA | trace | 1 |
| After 26 hour standing filtered through screen | | | | | | |
| 60 mesh | + | | NA | | + | |
| 100 mesh | trace | | NA | | trace | |
| 250 mesh | + | | NA | | trace | |

S = soluble;
IS = insoluble
− means no sediment;
+ means trace;
++ means more than trace < 1%;
+++ means 1-5%;
++++ means >5%
When observed under the microscpoe, after standing 24 hours and 20 inversions, no crystals were seen at 250×. The diluted samples were stirred and periodic observation under the microscope showed absence of crystals up to 5 hours from Run Number 23 and 10-100 crystals per view area from Run Number 25.
**2.5 g of concentrate were diluted with standard H₂O to 50 g.

TABLE 4

| Run No. | 26 | 27 | 28 | 29 | 30 | 31 | 32 | 33 |
|---|---|---|---|---|---|---|---|---|
| Composition wt. % | | | | | | | | |
| N-methyl-pyrrolidone (M-Pyrol) | 80 | − | 16 | 16 | − | 80 | − | 16 |
| N-octyl-pyrrolidone (LP-100) | − | 80 | 64 | 48 | 48 | − | 80 | 64 |
| N-dodceyl-pyrrolidone (LP-300) | − | − | − | 16 | − | − | − | − |

TABLE 4-continued

| | | | | | | | | |
|---|---|---|---|---|---|---|---|---|
| Butane diol | — | — | — | — | 32 | — | — | — |
| Gafac RE-610 | 5 | 5 | 5 | 5 | 5 | 5 | 5 | 5 |
| Igepal (CO-630) | 5 | 5 | 5 | 5 | 5 | — | — | — |
| Silwet (L-77) | — | — | — | — | — | 5 | 5 | 5 |
| Silwet (L-7607) | — | — | — | — | — | — | — | — |
| AAC: triforine | 10 | 10 | 10 | 10 | 10 | 10 | 10 | 10 |
| Solubility at 23°C. | S | S | S | S | IS | S | S | S |

Results:**

Bloom:

| | | | | | | | | | | | | | | | | |
|---|---|---|---|---|---|---|---|---|---|---|---|---|---|---|---|---|
| 0 time | excellent | | no emulsion | | poor | | poor | | NA | | excellent | | no emulsion | | no emulsion | |
| after 20 turns | excellent | | excellent | | excellent | | excellent | | NA | | excellent | | excellent | | excellent | |
| Solids, creams, or oil, mm: | SU-PER | PCPT | SU-PER | PCPT | SU-PER | PCPT | SU-PER | PCPT | SU-PER | PCPT | SU-PER | PCPT | SU-PER | PCPT | SU-PER | PCPT |
| 0 time | 0 | 2 | trace | 0 | 0 | 0 | trace | 0 | NA | NA | 0 | 3 | trace | 0 | 0 | 0 |
| 1 hour | 15 | 2 | 11 | 0 | 0 | 6 | 8 | 0 | NA | NA | 4 | 3 | 10 | 0 | 5 | 0 |
| 2 hours | 38 | 3 | 13 | 0 | 0 | 13 | 50 | 0 | NA | NA | 5 | 4 | 13 | 0 | 8 | 0 |
| 4 hours | 40 | 4 | 16 | 0 | 0 | 16 | 54 | 0 | NA | NA | 6 | 4 | 16 | 0 | 10 | 0 |
| 24 hours | 40 | 6 | 16 | 0 | 0 | 26 | 55 | 0 | NA | NA | 11 | 7 | 16 | 0 | 14 | 0 |

After 24 hour standing filtered through screen

| | | | | | | | | |
|---|---|---|---|---|---|---|---|---|
| 60 mesh | ++ | — | ++ | +++ | NA | +++ | — | — |
| 100 mesh | ++ | — | ++ | ++ | NA | ++ | — | — |
| 250 mesh | +++ | ++ | ++ | ++ | NA | +++ | ++ | ++ |

| Run No. | 34 | 35 | 36 | 37 | 38 | 39 | 40 | 41 |
|---|---|---|---|---|---|---|---|---|
| Composition wt. % | | | | | | | | |
| N-methyl-pyrrolidone (M-Pyrol) | 16 | — | 80 | — | 16 | 16 | — | 80 |
| N-octyl-pyrrolidone (LP-100) | 48 | 48 | — | 80 | 64 | 48 | 48 | — |
| N-dodceyl-pyrrolidone (LP-300) | 16 | — | — | — | — | 16 | — | — |
| Butane diol | — | 32 | — | — | — | — | 32 | — |
| Gafac RE-610 | 5 | 5 | 5 | 5 | 5 | 5 | 5 | 5 |
| Igepal (CO-630) | — | — | — | — | — | — | — | — |
| Silwet (L-77) | 5 | 5 | — | — | — | — | — | — |
| Silwet (L-7607) | — | — | 5 | 5 | 5 | 5 | 5 | — |
| Pegol (L-31) | — | — | — | — | — | — | — | 5 |
| AAC: triforine | 10 | 10 | 10 | 10 | 10 | 10 | 10 | 10 |
| Solubility at 23°C. | S | IS | S | S | S | S | IS | S |

Results:*

Bloom:

| | | | | | | | | | | | | | | | | |
|---|---|---|---|---|---|---|---|---|---|---|---|---|---|---|---|---|
| 0 time | poor | | NA | | excellent | | no emulsion | | poor | | poor | | NA | | excellent | |
| after 20 turns | excellent | | NA | | excellent | | excellent | | excellent | | excellent | | NA | | excellent | |
| Solids, creams, or oil, mm: | SU-PER | PCPT | SU-PER | PCPT | SU-PER | PCPT | SU-PER | PCPT | SU-PER | PCPT | SU-PER | PCPT | SU-PER | PCPT | SU-PER | PCPT |
| 0 time | trace | 0 | NA | NA | 0 | 3 | trace | 0 | 0 | 0 | trace | 0 | NA | NA | 0 | 1 |
| 1 hour | 9 | 0 | NA | NA | 23 | 3 | 6 | 0 | 3 | 0 | 9 | 0 | NA | NA | 0 | 5 |
| 4 hours | 34 | 0 | NA | NA | 64 | 9 | 15 | 0 | 11 | 0 | 11 | 0 | NA | NA | 15 | 7 |
| 24 hours | 37 | 0 | NA | NA | 60 | 10 | 16 | 0 | 15 | 0 | 48 | 0 | NA | NA | 50 | 11 |

After 24 hour standing filtered through screen

| | | | | | | | | |
|---|---|---|---|---|---|---|---|---|
| 60 mesh | +++ | NA | — | — | — | +++ | NA | ++ |
| 100 mesh | ++ | NA | ++ | — | ++ | — | NA | ++ |
| 250 mesh | ++ | NA | +++ | — | ++ | — | NA | +++ |

| Run No. | 42 | 43 | 44 | 45 | 46 | 47 | 48 | 49 |
|---|---|---|---|---|---|---|---|---|
| Composition wt. % | | | | | | | | |
| N-methyl- | — | 16 | 16 | — | 80 | — | 16 | 16 |

TABLE 4-continued

| | | | | | | | | |
|---|---|---|---|---|---|---|---|---|
| pyrrolidone (M-Pyrol) | | | | | | | | |
| N-octyl-pyrrolidone (LP-100) | 80 | 64 | 48 | 48 | — | 80 | 64 | 48 |
| N-dodceyl-pyrrolidone (LP-300) | — | — | 16 | — | — | — | — | 16 |
| Butane diol | — | — | — | 32 | — | — | — | — |
| Gafac RE-610 | 5 | 5 | 5 | 5 | 10 | 10 | 10 | 10 |
| Igepal (CO-630) | — | — | — | — | — | — | — | — |
| Silwet (L-77) | — | — | — | — | — | — | — | — |
| Silwet (L-7607) | — | — | — | — | — | — | — | — |
| Pegol (L-31) | 5 | 5 | 5 | 5 | — | — | — | — |
| AAC: triforine | 10 | 10 | 10 | 10 | 10 | 10 | 10 | 10 |
| Solubility at 23°C. | S | S | S | IS | S | S | S | S |
| Results:* | | | | | | | | |
| Bloom: | | | | | | | | |
| 0 time | none | poor | poor | NA | excellent | no emulsion | poor | poor |
| after 20 turns | excellent | excellent | excellent | NA | excellent | excellent | excellent | excellent |
| Solids, creams, or oil. mm: | SU-PER / PCPT | SU-PER / PCPT | SU-PER / PCPT | SU-PER / PCPT | SU-PER / PCPT | SU-PER / PCPT | SU-PER / PCPT | SU-PER / PCPT |
| 0 time | trace  0 | 0  0 | 0  0 | NA  NA | 0  0 | 2  0 | 0  trace | 0  0 |
| 1 hour | 10  0 | 3  0 | 7  0 | NA  NA | 0  1 | 8  0 | 0  5 | 5  0 |
| 4 hours | 13  0 | 10  0 | 11  0 | NA  NA | | No readings taken | | |
| 24 hours | 16  0 | 11  0 | 42  0 | NA  NA | 0  15 | 15  0 | 0  14 | 11  0 |
| After 24 hour standing filtered through screen | | | | | | | | |
| 60 mesh | — | — | ++ | NA | ++ | — | — | +++ |
| 100 mesh | — | — | — | NA | ++ | — | ++ | ++ |
| 250 mesh | — | — | — | NA | +++ | ++ | — | ++ |

S = soluble;
IS = insoluble;
— means no sediment;
+ means trace;
++ means more than trace < 1%;
+++ means 1-5%
**2.5 g of concentrate were diluted with standard H₂O to 50 g.

TABLE 4A

MICROSCOPIC CRYSTAL GROWTH OBSERVATION FOR SELECTED FORMULATIONS

| Run No. | 27 | 32 | 33 | 36 | 37 | 38 |
|---|---|---|---|---|---|---|
| Microscopic observation under stirring for crystal growth, 250× Time: | | | | | | |
| 0 hour | 0 | 0 | 0 | ** | 0 | 0 |
| 1 hour | 0 | 0 | 0 | ** | 0 | 0 |
| 4 hours | 0 | 0 | 0 | ** | 0 | *** |
| 20 hours | *** | ** | *** | *** | * | *** |
| 25 hours | *** | ** | *** | *** | * | *** |
| After 25 hour stirring filtered through screen | | | | | | |
| 60 mesh | — | — | — | — | — | — |
| 100 mesh | — | + | — | + | — | — |
| 250 mesh | — | — | — | — | — | — |

| Run No. | 39 | 42 | 43 | 44 | 47 | 48 |
|---|---|---|---|---|---|---|
| Microscopic ovservation under stirring for crystal growth, 250× Time: | | | | | | |
| 0 hour | 0 | 0 | 0 | 0 | 0 | 0 |
| 1 hour | 0 | 0 | 0 | 0 | 0 | 0 |
| 4 hours | *** | *** | 0 | ** | *** | *** |
| 20 hours | *** | *** | *** | *** | *** | ** |
| 25 hours | *** | *** | *** | *** | *** | ** |
| After 25 hour stirring filtered through screen | | | | | | |
| 60 mesh | — | — | — | — | — | — |
| 100 mesh | — | — | + | — | + | — |
| 250 mesh | + | + | — | + | + | — |

TABLE 5

| Run No. | 50 | 51 | 52 | 53 | 54 | 55 | 56 | 57 |
|---|---|---|---|---|---|---|---|---|
| Composition wt. % | | | | | | | | |
| N-methyl-pyrrolidone (M-Pyrol) | 0 | 0 | 0 | 0 | 0 | 80 | 80 | 80 |

TABLE 5-continued

| | | | | | | | | |
|---|---|---|---|---|---|---|---|---|
| N-octyl-pyrrolidone (LP-100) | 80 | 80 | 80 | 80 | 80 | 0 | 0 | 0 |
| N-dodceyl-pyrrolidone (LP-300) | 0 | 0 | 0 | 0 | 0 | 0 | 0 | 0 |
| Gafac RE-610 | 5 | 5 | 5 | 5 | 10 | 5 | 5 | 5 |
| Igepal (CO-630) | 5 | 0 | 0 | 0 | 0 | 5 | 0 | 0 |
| Silwet (L-77) | 0 | 5 | 0 | 0 | 0 | 0 | 5 | 0 |
| Silwet (L-7607) | 0 | 0 | 5 | 0 | 0 | 0 | 0 | 5 |
| Pegol (L-31) | 0 | 0 | 0 | 5 | 0 | 0 | 0 | 0 |
| AAC: Sevin | 10 | 10 | 10 | 10 | 10 | 10 | 10 | 10 |

Results:**

Bloom:

| | | | | | | | | | | | | | | | | |
|---|---|---|---|---|---|---|---|---|---|---|---|---|---|---|---|---|
| 0 time | none | | none | | none | | none | | none | | good | | excellent | | excellent | |
| after 20 turns | excellent | | excellent | | excellent | | excellent | | excellent | | excellent | | excellent | | excellent | |
| Solids, creams, or oil. mm: | SUPER | PCPT | SUPER | PCPT | SUPER | PCPT | SUPER | PCPT | SUPER | PCPT | SUPER | PCPT | SUPER | PCPT | SUPER | PCPT |
| 0 time | 0 | 0 | 0 | 0 | 0 | 0 | 0 | 0 | 0 | 0 | 0 | 0 | 0 | 0 | 0 | 0 |
| 1 hour | 11 | 0 | 11 | 0 | 11 | 0 | 9 | 0 | 4 | 0 | 0 | 5 | 0 | 5 | 0 | 5 |
| 2 hours | 12 | 0 | 12 | 0 | 13 | 0 | 11 | 0 | 6 | 0 | 0 | 5 | 0 | 5 | 0 | 5 |
| 4 hours | 13 | 0 | 14 | 0 | 13 | 0 | 13 | 0 | 8 | 0 | 0 | 5 | 0 | 5 | 0 | 5 |
| 24 hours | 15 | 0 | 14 | 0 | 13 | 0 | 13 | 0 | 13 | 0 | 0 | 5 | 0 | 5 | 0 | 5 |

After 24 hour standing filtered through screen

| | | | | | | | | |
|---|---|---|---|---|---|---|---|---|
| 60 mesh | — | — | — | — | — | — | — | — |
| 100 mesh | — | — | — | — | — | + | ++ | ++ |
| 250 mesh | — | — | — | — | — | +++ | ++ | ++ |

| Run No. | 58 | 59 | 60 | 61 | 62 | 63 | 64 | 65 |
|---|---|---|---|---|---|---|---|---|

Composition wt. %

| | | | | | | | | |
|---|---|---|---|---|---|---|---|---|
| N-methyl-pyrrolidone (M-Pyrol) | 80 | 80 | 32 | 32 | 32 | 32 | 32 | 16 |
| N-octyl-pyrrolidone (LP-100) | 0 | 0 | 48 | 48 | 48 | 48 | 48 | 64 |
| N-dodceyl-pyrrolidone (LP-300) | 0 | 0 | 0 | 0 | 0 | 0 | 0 | 0 |
| Gafac RE-610 | 5 | 10 | 5 | 5 | 5 | 5 | 10 | 5 |
| Igepal (CO-630) | 0 | 0 | 5 | 0 | 0 | 0 | 0 | 5 |
| Silwet (L-77) | 0 | 0 | 0 | 5 | 0 | 0 | 0 | 0 |
| Silwet (L-7607) | 0 | 0 | 0 | 0 | 5 | 0 | 0 | 0 |
| Pegol (L-31) | 5 | 0 | 0 | 0 | 0 | 5 | 0 | 0 |
| AAC: Sevin | 10 | 10 | 10 | 10 | 0 | 10 | 10 | 10 |

Results:**

Bloom:

| | | | | | | | | | | | | | | | | |
|---|---|---|---|---|---|---|---|---|---|---|---|---|---|---|---|---|
| 0 time | excellent | | excellent | | poor | | poor | | poor | | poor | | poor | | poor | |
| after 20 turns | excellent | | excellent | | excellent | | excellent | | excellent | | excellent | | excellent | | excellent | |
| Solids, creams, or oil. mm: | SUPER | PCPT | SUPER | PCPT | SUPER | PCPT | SUPER | PCPT | SUPER | PCPT | SUPER | PCPT | SUPER | PCPT | SUPER | PCPT |
| 0 time | 0 | 0 | 0 | 0 | 0 | 0 | 0 | 0 | 0 | 0 | 0 | 0 | 0 | 0 | 0 | 0 |
| 1 hour | 0 | 5 | 0 | 4 | 6 | 0 | 3 | 0 | 3 | 0 | 1 | 0 | 0 | 0 | 9 | 0 |
| 2 hours | 0 | 5 | 0 | 5 | 7 | 0 | 6 | 0 | 5 | 0 | 3 | 0 | 0 | 0 | 10 | 0 |
| 4 hours | 0 | 5 | 0 | 5 | 7 | 0 | 7 | 0 | 7 | 0 | 4 | 0 | trace | 0 | 12 | 0 |
| 24 hours | 0 | 5 | 0 | 5 | 7 | 0 | 10 | 0 | 9 | 0 | 8 | 0 | 8 | 0 | 12 | 0 |

After 24 hour standing filtered through screen

| | | | | | | | | |
|---|---|---|---|---|---|---|---|---|
| 60 mesh | — | — | — | — | — | — | — | — |
| 100 mesh | + | ++ | — | — | — | — | — | — |
| 250 mesh | +++ | ++ | — | — | — | — | — | — |

| Run No. | 66 | 67 | 68 | 69 | 70 |
|---|---|---|---|---|---|

Composition wt. %

| | | | | | |
|---|---|---|---|---|---|
| N-methylpyrrlidone (M-Pyrol) | 16 | 16 | 16 | 16 | 16 |

TABLE 5-continued

| | | | | | |
|---|---|---|---|---|---|
| N-octylpyrrolidone (LP-100) | 64 | 64 | 64 | 64 | 48 |
| N-dodceylpyrrolidone (LP-300) | 0 | 0 | 0 | 0 | 16 |
| Gafac RE-610 | 5 | 5 | 5 | 10 | 5 |
| Igepal (CO-630) | 0 | 0 | 0 | 0 | 5 |
| Silwet (L-77) | 5 | 0 | 0 | 0 | 0 |
| Silwet (L-7607) | 0 | 5 | 0 | 0 | 0 |
| Pegol (L-31) | 0 | 0 | 5 | 0 | 0 |
| AAC: Sevin | 10 | 10 | 0 | 10 | 10 |
| Results:** | | | | | |
| Bloom: | | | | | |
| 0 time | none | none | none | none | none |
| after 20 turns | excellent | excellent | excellent | excellent | excellent |

| Solids, creams or oil, mm: | SUPER | PCPT | SUPER | PCPT | SUPER | PCPT | SUPER | PCPT | SUPER | PCPT |
|---|---|---|---|---|---|---|---|---|---|---|
| 0 time | 0 | 0 | 0 | 0 | 0 | 0 | 0 | 0 | 0 | 0 |
| 1 hour | 4 | 0 | 7 | 0 | 5 | 0 | 3 | 0 | 9 | 0 |
| 2 hours | 5 | 0 | 8 | 0 | 6 | 0 | 6 | 0 | 9 | 0 |
| 4 hours | 6 | 0 | 9 | 0 | 8 | 0 | 10 | 0 | 9 | 0 |
| 24 hours | 11 | 0 | 11 | 0 | 10 | 0 | 11 | 0 | 10 | 0 |
| After 24 hour standing filtered through screen | | | | | | | | | | |
| 60 mesh | — | | — | | — | | — | | — | |
| 100 mesh | — | | — | | — | | — | | — | |
| 250 mesh | — | | — | | — | | — | | — | |

| | Run No. | 71 | 72 | 73 | 74 |
|---|---|---|---|---|---|
| | Composition wt. % | | | | |
| | N-methylpyrrlidone (M-Pyrol) | 16 | 16 | 16 | 16 |
| | N-octylpyrrolidone (LP-100) | 48 | 48 | 48 | 48 |
| | N-dodceylpyrrolidone (LP-300) | 16 | 16 | 16 | 16 |
| | Gafac RE-610 | 5 | 5 | 5 | 10 |
| | Igepal (CO-630) | 0 | 0 | 0 | 0 |
| | Silwet (L-77) | 5 | 0 | 0 | 0 |
| | Silwet (L-7607) | 0 | 5 | 0 | 0 |
| | Pegol (L-31) | 0 | 0 | 5 | 0 |
| | AAC: Sevin | 10 | 10 | 10 | 10 |
| | Results:** | | | | |
| | Bloom: | | | | |
| | 0 time | none | none | none | none |
| | after 20 turns | excellent | excellent | excellent | excellent |

| Solids, creams or oil, mm: | SUPER | PCPT | SUPER | PCPT | SUPER | PCPT | SUPER | PCPT |
|---|---|---|---|---|---|---|---|---|
| 0 time | 0 | 0 | 0 | 0 | 0 | 0 | 0 | 0 |
| 1 hour | 7 | 0 | 11 | 0 | 5 | 0 | 3 | 0 |
| 2 hours | 7 | 0 | 11 | 0 | 6 | 0 | 5 | 0 |
| 4 hours | 9 | 0 | 11 | 0 | 7 | 0 | 8 | 0 |
| 24 hours | 10 | 0 | 11 | 0 | 10 | 0 | 10 | 0 |
| After 24 hour standing filtered through screen | | | | | | | | |
| 60 mesh | — | | — | | — | | — | |
| 100 mesh | — | | — | | — | | — | |
| 250 mesh | — | | — | | — | | — | |

− means no sediment;
+ means trace;
++ means more than trace < 1%;
+++ means 1-5%
**2.5 g of concentrate were diluted with standard H₂O to 50 g.

TABLE 5A
MICROSCOPIC CRYSTAL GROWTH OBSERVATION FOR SELECTED FORMULATIONS

| Run No. | 50 | 51 | 52 | 53 | 54 | 55 | 56 | 57 |
|---|---|---|---|---|---|---|---|---|
| Microscopic observation under stirring for crystal growth, 250× Time: | | | | | | | | |
| 0 hour | 0 | 0 | 0 | 0 | 0 | * | * | * |
| 1 hour | 0 | 0 | 0 | 0 | 0 | * | * | * |
| 2 hours | 0 | 0 | 0 | 0 | 0 | * | * | * |
| 4 hours | 0 | 0 | 0 | 0 | 0 | * | * | * |
| 24 hours | 0 | 0 | 0 | 0 | 0 | * | * | * |
| After 25 hour stirring filtered through screen | | | | | | | | |
| 60 mesh | — | — | — | — | — | — | — | — |
| 100 mesh | — | — | — | — | — | — | ++ | ++ |
| 250 mesh | — | — | — | — | — | ++ | ++ | ++ |

| Run No. | 58 | 59 | 60 | 61 | 62 | 63 | 64 | 65 |
|---|---|---|---|---|---|---|---|---|
| Microscopic observation under stirring for crystal growth, 250× Time: | | | | | | | | |
| 0 hour | * | * | 0 | 0 | 0 | 0 | 0 | 0 |
| 1 hour | * | * | 0 | 0 | 0 | 0 | 0 | 0 |
| 2 hours | * | * | 0 | 0 | 0 | 0 | 0 | 0 |
| 4 hours | * | * | 0 | 0 | 0 | 0 | 0 | 0 |
| 24 hours | * | * | 0 | * | * | 0 | * | * |
| After 25 hour stirring | | | | | | | | |

TABLE 5A-continued

MICROSCOPIC CRYSTAL GROWTH
OBSERVATION FOR SELECTED FORMULATIONS

| filtered through screen | | | | | | | | | |
|---|---|---|---|---|---|---|---|---|---|
| 60 mesh | — | — | — | — | — | — | — | — | |
| 100 mesh | ++ | + | — | — | — | — | — | — | |
| 250 mesh | ++ | +++ | — | — | — | — | — | — | |
| Run No. | 66 | 67 | 68 | 69 | 70 | 71 | 72 | 73 | 74 |
| Microscopic observation under stirring for crystal growth, 250× Time: | | | | | | | | | |
| 0 hour | 0 | 0 | 0 | 0 | 0 | 0 | 0 | 0 | 0 |
| 1 hour | 0 | 0 | 0 | 0 | 0 | 0 | 0 | 0 | 0 |
| 2 hours | 0 | 0 | 0 | 0 | 0 | 0 | 0 | 0 | 0 |
| 4 hours | 0 | 0 | 0 | 0 | 0 | 0 | 0 | 0 | 0 |
| 24 hours | * | 0 | 0 | 0 | 0 | 0 | 0 | 0 | ** |
| After 24 hour stirring filtered through screen | | | | | | | | | |
| 60 mesh | — | — | — | — | — | — | — | — | — |
| 100 mesh | — | — | — | — | — | — | — | — | — |
| 250 mesh | — | — | — | — | + | — | — | — | — |

What is claimed is:

1. A stable emulsifiable concentrate consisting essentially of a herbicide which is substantially insoluble in water, a surfactant and a biodegradable solvent selected from the group consisting of a first component, a second component, and combinations thereof, said first component being selected from the group consisting of pyrrolidones having the formula

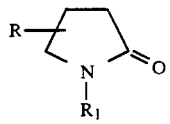

wherein R is hydrogen or lower alkyl and $R_1$ is lower alkyl, cyclic lactones, lower alkyl cyclic carbonates, lower alkyl imidazolone, lower alkylamides of formic and acetic acid, and lower alkyl sulfoxides, wherein lower alkyl is an alkyl group having from 1 to 4 carbon atoms, and being present in an amount effective to solubilize the herbicide, and said second component being selected from the group consisting of pyrrolidones having the formula

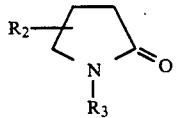

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14; alkyl gamma-butyrolactones, alkyl cyclic carbonates, and combinations thereof, wherein the alkyl portion may be distributed at one or more sites on the ring so long as one portion contains at least 6 carbon atoms and the total number of alkyl carbon atoms does not exceed 14, and having an HLB value of from about 2 to 8, and being present in an amount, in conjunction with a surfactant, effective to disperse the herbicide.

2. The concentrate of claim 1 wherein the first component is selected from the group consisting of N-methylpyrrolidone, ethylene carbonate, propylene carbonate, butylene carbonate, N-N,dimethylimidazolone, dimethyl formamide and dimethylacetamide, dimethylsulfoxide, and mixtures thereof.

3. The concentrate of claim 1 wherein the second component is selected from the group consisting of N-octylpyrrolidone, N-dodecylpyrrolidone, N-2-ethylhexylpyrrolidone).

4. The concentrate of claim 3 wherein first component is N-methylpyrrolidone.

5. The concentrate of claim 4 wherein the second component is N-octylpyrrolidone.

6. The concentrate of claim 1 wherein the agriculturally active chemical is a herbicide selected from the group consisting of phenoxy compounds, benzoic acid, acetic acid, phthalic acid, aniline derivatives, nitriles, amides, acetamides, anilides, carbamates, thiocarbamates, heterocyclic nitrogen derivatives, urea derivatives, and phosphates.

7. The concentrate of claim 1 the amount of solvent is in the range from about 20 to 90%, the remaining components constituting 80 to 10%, each amount being based on the total weight of the concentrate.

8. The concentrate of claim 7 wherein the amount of the first component is from about 0 to 95% and the amount of the second component is from about 5 to 100% by weight based on the weight of the concentrate.

9. The concentrate of claim 8 wherein the amount of surfactant is from about 1 to 25% by weight based on the total weight of the concentrate.

10. The concentrate of claim 9 wherein the concentration of the herbicide is in excess of about 5 weight percent, based on the weight of the total concentrate.

11. The concentrate of claim 10 wherein the amount of the herbicide is from about 5% to 25% by weight based on the total weight of the concentrate.

12. A composition comprising the emulsifiable concentrate of claim 1 and water wherein the herbicide is present in an effective herbicidal active amount.

13. A method for treatment of plants comprising applying to said plant or the soil surrounding said plant the composition of claim 12.

14. A method of treatment of pests on animals comprising applying to said animal the composition of claim 12.

15. A method of controlling the population of agricultural pests by applying to the pests the composition of claim 12.

16. The method of claim 15 wherein the pests are microorganisms.

* * * * *